(12) United States Patent
Magnani et al.

(10) Patent No.: US 8,734,787 B2
(45) Date of Patent: May 27, 2014

(54) DRUG DELIVERY SYSTEM

(75) Inventors: Mauro Magnani, Urbino (IT); Luigia Rossi, Urbino (IT); Sara Biagiotti, Tavullia (IT); Marzia Bianchi, Fossombrone (IT)

(73) Assignee: Erydel S.p.A., Urbino (IT)

( * ) Notice: Subject to any disclaimer, the term of this patent is extended or adjusted under 35 U.S.C. 154(b) by 15 days.

(21) Appl. No.: 13/375,890

(22) PCT Filed: Jun. 7, 2010

(86) PCT No.: PCT/EP2010/003783
§ 371 (c)(1),
(2), (4) Date: Feb. 23, 2012

(87) PCT Pub. No.: WO2010/145849
PCT Pub. Date: Dec. 23, 2010

(65) Prior Publication Data
US 2012/0141540 A1 Jun. 7, 2012

(30) Foreign Application Priority Data

Jun. 5, 2009 (GB) .................................. 0909754.4

(51) Int. Cl.
*A61K 35/18* (2006.01)
*C12N 5/078* (2010.01)
*A61K 38/13* (2006.01)

(52) U.S. Cl.
CPC .............. *C12N 5/0641* (2013.01); *A61K 35/18* (2013.01); *A61K 38/13* (2013.01); *Y10S 424/81* (2013.01); *Y10S 514/855* (2013.01)
USPC ........ 424/93.73; 424/533; 424/577; 424/810; 514/19.3; 514/21.2; 514/855; 435/372

(58) Field of Classification Search
None
See application file for complete search history.

(56) References Cited

U.S. PATENT DOCUMENTS

| 5,605,828 | A | * | 2/1997 | Glenn | ........................... 435/236 |
| 5,622,963 | A | * | 4/1997 | Armstrong et al. | ........... 514/291 |
| 5,767,069 | A | * | 6/1998 | Ko et al. | ...................... 514/20.5 |
| 6,887,842 | B1 | | 5/2005 | Briesewitz et al. | |
| 2003/0215454 | A1 | * | 11/2003 | Colb et al. | .................. 424/175.1 |
| 2004/0010309 | A1 | * | 1/2004 | Seward et al. | ............... 623/1.42 |
| 2009/0053245 | A1 | | 2/2009 | Mutz et al. | |

OTHER PUBLICATIONS

The Merck Manual of Diagnosis and Therapy, 17th edition, editors Beers and Berkow, 1999, Merck Research Laboratories, pp. 886-888.*
Woo et al., Bone Marrow Transplant. Dec. 1997;20(12):1095-8.*
Donia et al., Br J Clin Pharmacol. Dec. 2010;70(6):784-93. doi: 10.1111/j.1365-2125.2010.03735.x.*
Lynch et al., Am J Hematol. 1980;9(3):249-59.*
Patel et al., Current Pharmaceutical Design, 2008, 14:63-70.*
Gutierrez Millan et al., Journal of Controlled Release, 2004, 95:27-49.*
PCT Search Report for Application No. PCT/EP2010/003783, Oct. 12, 2011.

* cited by examiner

*Primary Examiner* — Michael Szperka
(74) *Attorney, Agent, or Firm* — Quine Intellectual Property Law Group, P.C.

(57) ABSTRACT

Red blood cells can be used as effective drug delivery systems when they contain proteins that do not readily diffuse out and which form affinity complexes with the desired drug.

20 Claims, 8 Drawing Sheets pET-45b(+)-FKBP12 construct

SDS-PAGE of BL21(DE3) homogenates

Characterization of purified FKBP12 a) SDS-PAGE b) immunoblotting

Dot blot analysis of rFKBP12-FK506 binding

Cell recovery

Survival curves of FKBP12-loaded RBC

FKBP12-loaded RBC binding capacity for Tacrolimus

Recombinant FKBP12 concentration into engineered RBC

CsA and CsD HPLC chromatogram

SDS-PAGE of induced BL21(DE3) homogenates and of purified CypA a) SDS-PAGE b) immunoblot 125I-CypA intra-erythrocytic concentration and CsA binding capacity of CypA-loaded RBC

SEQUENCE LISTING

```
<160> NUMBER OF SEQ ID NOS: 6

<210> SEQ ID NO 1
<211> LENGTH: 32
<212> TYPE: DNA
<213> ORGANISM: artificial
<220> FEATURE:
<223> OTHER INFORMATION: PCR Primer

<400> SEQUENCE: 1
tccgcccacg tgatgggagt gcaggtggaa ac                              32
```

```
<210> SEQ ID NO 2
<211> LENGTH: 32
<212> TYPE: DNA
<213> ORGANISM: artificial
<220> FEATURE:
<223> OTHER INFORMATION: PCR Primer

<400> SEQUENCE: 2
gaggccagga tcctcattcc agttttagaa gc                                   32

<210> SEQ ID NO 3
<211> LENGTH: 354
<212> TYPE: DNA
<213> ORGANISM: artificial
<220> FEATURE:
<223> OTHER INFORMATION: 6His-FKBP12

<400> SEQUENCE: 3
atggcacatc accaccacca tcacgtgatg ggagtgcagg tggaaaccat ctccccagga     60
gacgggcgca ccttccccaa gcgcggccag acctgcgtgg tgcactacac cgggatgctt   120
gaagatggaa agaaatttga ttcctcccgg gacagaaaca gcccctttaa gtttatgcta   180
ggcaagcagg aggtgatccg aggctgggaa gaggggttg cccagatgag tgtgggtcag    240
agagccaaac tgactatatc tccagattat gcctatggtg ccactgggca cccaggcatc   300
atcccaccac atgccactct cgtcttcgat gtggagcttc taaaactgga atga          354

<210> SEQ ID NO 4
<211> LENGTH: 33
<212> TYPE: DNA
<213> ORGANISM: artificial
<220> FEATURE:
<223> OTHER INFORMATION: PCR Primer

<400> SEQUENCE: 4
tattagccca cgtgaacccc accgtgttct tcg                                  33

<210> SEQ ID NO 5
<211> LENGTH: 31
<212> TYPE: DNA
<213> ORGANISM: artificial
<220> FEATURE:
<223> OTHER INFORMATION: PCR Primer

<400> SEQUENCE: 5
aacacaaggg atccttattc gagttgtcca c                                    31

<210> SEQ ID NO 6
<211> LENGTH: 519
<212> TYPE: DNA
<213> ORGANISM: artificial
<220> FEATURE:
<223> OTHER INFORMATION: N-terminal His-tagged CypA

<400> SEQUENCE: 6
atggcacatc accaccacca tcacgtgaac cccaccgtgt tcttcgacat tgccgtcgac     60
ggcgagccct gggccgcgt ctcctttgag ctgtttgcag acaaggtccc aaagacagca    120
gaaaattttc gtgctctgag cactggagag aaaggatttg gttataaggg ttcctgcttt    180
cacagaatta ttccagggtt tatgtgtcag ggtggtgact tcacacgcca taatggcact    240
ggtggcaagt ccatctatgg ggagaaattt gaagatgaga acttcatcct aaagcatacg    300
ggtcctggca tcttgtccat ggcaaatgct ggacccaaca caaatggttc ccagtttttc    360
```

```
atctgcactg ccaagactga gtggttggat ggcaagcatg tggtgtttgg caaagtgaaa      420
gaaggcatga atattgtgga ggccatggag cgctttgggt ccaggaatgg caagaccagc      480
aagaagatca ccattgctga ctgtggacaa ctcgaataa                             519
```

DRUG DELIVERY SYSTEM

CROSS-REFERENCE TO RELATED APPLICATIONS

This application is a 371 application of PCT/EP2010/003783, Drug Delivery Systems, by Mauro Magnani, et al., filed Jun. 7, 2010, which claims priority to and benefit of GB Patent Application 0909754.4, filed Jun. 5, 2009. The full disclosure of the prior application is incorporated herein by reference.

The present invention relates to the use of red blood cells as drug delivery vehicles, and to methods for producing same.

INTRODUCTION

Erythrocytes, also known as red blood cells (RBCs), are typically used for transfusions to replace lost blood. In addition to this well known use, RBCs are now being used in a number of newer applications, both as therapeutics and as diagnostic agents. Most of these applications are possible because of the peculiar property of these cells that allows them to be opened and resealed without affecting their main properties or in vivo circulation. The technology to achieve this is described in U.S. Pat. No. 6,139,836 and EP-A-882448, and allows the procedure to be performed in the clinic, with minimal amounts of patient blood, to yield processed RBCs.

The biomedical use of these processed RBCs are numerous and include the possibility of engineering the same by the addition of drugs, biologics and/or nanomaterials. These constructs provide a significant addition to the armoury available to physicians for the release of drugs in circulation, for targeting drugs to selected sites in the body, or for in vivo diagnostic procedures based on magnetic and/or optical methods.

Autologous human RBC loaded with corticosteroid analogues have been used in the treatment of Cystic Fibrosis, Crohn disease, Ulcerative Colitis and COPD patients. Based on these results, the E.M.E.A. has granted the designation of "Orphan Drug" to "Dexamethasone Sodium Phosphate for encapsulation in human erythrocytes for treatment of Cystic Fibrosis" (Orphan Drug Designation EMEA/OD/039/04-EU/3/04/230).

The encapsulation of superparamagnetic nanoparticles within RBCs has lead to the generation of new biomimetic constructs that now permit the use of these nanomaterials in vivo, avoiding their rapid sequestration and their accumulation in unwanted areas (WO 2008/003524).

Similarly, the encapsulation of infrared fluorescent agents into RBC has opened the way to the measurement of vasomotion in human retinal vasculature, suggesting a possible correlation with retinal oedema [Macula 2009 meeting in NYC].

One limitation in the use of RBCs as carriers for drugs is the permeability of the RBC membrane. Once the selected drug has been encapsulated using a procedure as described above, there are three possibilities:

The drug is indefinitely retained within the RBC because it is not transported by, or does not diffuse out of, the membrane and remains in circulation for as long as the loaded RBC remains intact;

The drug is immediately released by the loaded RBC because it can easily diffuse through the RBC membrane; or The drug may be non-diffusible, remaining within the RBC until it is converted into a diffusible form, such as dexamethasone-21-phosphate, which remains until the phosphate group is hydrolysed to form dexamethasone.

Thus, drug delivery using erythrocytes is a technological platform which lends itself to a wide range of applications, but which suffers from an inherent inability to control the release of substances transported by the processed RBCs.

It has now, surprisingly, been found that it is possible to use RBCs as drug delivery vehicles for diffusible drugs, by incorporating proteins into the RBCs that have an affinity for the drug and which do not readily diffuse out of the RBC. In other words, we have found that Red Blood Cells can be used as effective drug delivery systems when they contain proteins that do not readily diffuse out and which form affinity complexes with the desired drug. It is also envisaged that Red Blood Cells loaded with proteins able to form affinity complexes with selected drugs could be also administered to a human as an antidote in case of toxicity caused by the accidental consumption of an amount of drug higher than expected.

SUMMARY OF THE INVENTION

Thus, in a first aspect, the present invention provides a red blood cell containing an association complex comprising a drug and a protein, wherein the uncomplexed form of the drug is capable of readily passing the red blood cell membrane and wherein the uncomplexed protein cannot readily pass the red blood cell membrane.

Also provided is a red blood cell containing a protein that cannot readily pass the red blood cell membrane and which can form an association complex with a target drug, the uncomplexed form of the drug being capable of readily passing the red blood cell membrane.

Preferably, the protein, or an analogue thereof, occurs in wild type red blood cells and is present at elevated levels. Wild type RBCs are those found naturally occurring in a patient or the population, before any modification. Suitable RBCs may be the patient's own, where the patient is known, or may be from any suitable source. A preferred source is a universal donor (blood group O, Rhesus negative).

RBCs are preferably unmodified, other than to introduce the protein. Where they are modified, they may suitably be modified to prevent the escape of the protein, for example, or to allow the escape of the drug. The former may be by blocking escape routes, such as transporter proteins, or by blocking enzymes capable of catabolising the protein, while the latter may be by permeabilising the membrane or transforming the RBC to express or incorporate a membrane transporter of the drug.

The RBC may be engineered to express the protein. In the event that the protein is already expressed in the RBC, such engineering may be by amplifying the number of genes, or by increasing mRNA transcription rates, such as by using a greater copy number promoter.

Mature RBCs do not continue to express proteins, and it may not be desirable to express large amounts of carrier protein prior to the intended use. Transformation also requires a reproductive system and generally a host, so will not usually be suitable for general treatment. Accordingly, it is preferred to open the RBC, as described in U.S. Pat. No. 6,139,836 (incorporated herein by reference), for example, introduce the carrier protein, and then reseal the RBC. The resulting, processed RBC may then be exposed to the drug. As the drug may pass the RBC membrane, it can then form an association complex with the carrier protein and the RBCs may then be used for any intended therapy.

It will be appreciated that, in this embodiment, the RBC may already express the carrier protein, but that additional carrier protein may be incorporated, in order to increase the carrying capacity of the RBC for the drug. It has been found that such an increase is generally directly proportional to the amount of extra protein added. In this regard, RBCs are surprisingly resilient to changes in protein content, so that amounts of carrier protein may be raised as high as 5% w/w, or up to about 10× naturally occurring levels if this does not exceed 5 w/w.

Preferably, the RBC may consist solely of the protein, i.e. with all membrane proteins removed, although the presence of haemoglobin is preferred.

The protein may be an analogue, mutant, or variant of a naturally occurring protein. It may be engineered for ease of expression or harvesting, to enhance or reduce drug affinity, or to express just those units responsible for drug binding, or to express multiple drug-binding units as one protein, for example. Chimaeric proteins are also preferred.

By 'association complex' is meant that the drug and protein will be attracted together in situ. This attraction should be sufficient to allow the RBC to act as a reservoir of drug, but not so strong as to effectively take the drug out of solution altogether. The dissociation constant should be such that it is possible to achieve therapeutic levels of drug with transfusions of between 50 ml and 500 ml of processed blood, preferably within 5 minutes and 2 hours of transfusion. Suitable Kd values may be in the range of $10^4$ to $10^9 M^{-1}$.

The protein should not be able to readily pass the RBC membrane. Owing to size, it is generally possible to prevent passage of protein across the membrane substantially completely. If this is not possible, then no more than 50% of the protein should be able to escape within 24 hours, but it is preferred to reduce this to no more than 5%, and preferably no more than 1%. The amount of entrapped protein that is released could be measured in different ways known in the art, for example by using immunochemical methods (i.e. ELISA assays), radioimmunochemical assays, or by detecting the protein by measuring its biological activity (in case the entrapped protein is an enzyme, for instance).

The drug should be able to pass the membrane, and it is preferred that this free passage, or facilitated, such as by suitable channels or transporters, or by poration of the RBC. The latter is not preferred, as it can have a deleterious effect on the RBC.

There is no particular limit on the nature of the drug, provided that it can pass the RBC membrane. For ease of production, it is preferred that the drug be able to pass the membrane of an unmodified RBC. The drug may be a well known drug, or a form modified to be able to pass an RBC membrane. The latter is generally less preferred, as there may be an effect on drug activity. This concept is illustrated herein by a number of non-limiting examples.

The protein, preferably an immunophillin, and the drug are able to associate. The associated drug is preferably capable of binding said protein (for instance an immunophillin) to the extent that encapsulation within RBCs is possible, as described herein. Furthermore, many drugs are known to have binding partners that associate with them, such as FKBP12 and FK506, or Cyclosporine and Cyclophilin. Such combinations are preferred. However, we have also shown that rapamycin can associate with FKBP 12 and be useful in this invention. The present invention therefore encompasses all drug and their associated protein binding partners where the uncomplexed form of the drug is capable of readily passing the red blood cell membrane and wherein the uncomplexed protein cannot readily pass the red blood cell membrane.

The drugs may also be immunosuppressive and/or antiviral agents. For instance, cyclosporine and its derivatives are used to treat HCV. The drug may also be an anti-cancer agent. For instance rapamycin is used to treat tumour cells. The immunosuppressant is preferably capable of inhibiting the activation of the phosphatase calcineurin by forming a complex with calcineurin and the immunophillin. Thus, the immunophillin is preferably selected from FKBP12 (or its analogues), or Cyclophilin (or its analogues) and the immunosuppressant is a calcineurin inhibitor. The calcineurin inhibitor is preferably selected from FK506 or Cyclosporine.

Thus, the drug is preferably rapamycin or its analogues, and most preferably FK506 or its analogues. In these instances, it is preferred that the associated protein is FKBP 12 or its analogues. The drug may also, preferably, be Cyclosporine or its analogues and in this instance it is preferred that the associated protein is Cyclophilin or its analogues.

There is further provided an RBC as defined above, but containing little or no drug. The drug may be added at, or closer to, the time of administration. This may be helpful if extended exposure to the drug is deleterious in any way to the RBC, or where the drug has a limited life once it has been exposed to RBCs, for example.

Methods for the treatment or prophylaxis of cancer or viruses or methods of immunosuppression comprising administering the present RBCs to patients in need thereof are also envisaged.

Also provided is a method of reducing the concentration of a selected drug in a patient's body fluid, preferably the plasma, comprising administering Red Blood Cells loaded with associated proteins able to form affinity complexes with the selected drug. The selected drug will be taken up by forming a complex with the drug, thereby reducing the drug's activity or bio-availability and thus its toxicity. The toxicity may be caused by the accidental consumption of an amount of the selected drug higher than expected, thus a method of treating an overdose is preferred. Preferably, small amounts of the protein-loaded RBC are administered and the dose is gradually increased whilst levels of the drug are monitored, for instance by assaying the body fluid regularly.

The invention will now be described in more detail with reference to the accompanying Figures.

a) Lane 1: LMW standard, lane 2-4: CypA. 1.0, 2.5 and 5.0 µg of purified CypA were subjected to electrophoretic run on 15% polyacrylamide gel followed by Coomassie Blue staining and densitometric assay to verify the protein molecular weight and purity level. b) Protein bands were transferred onto a 0.2 µm nitrocellulose membrane and immunoblotted to verify the protein identity.

Figure 11:
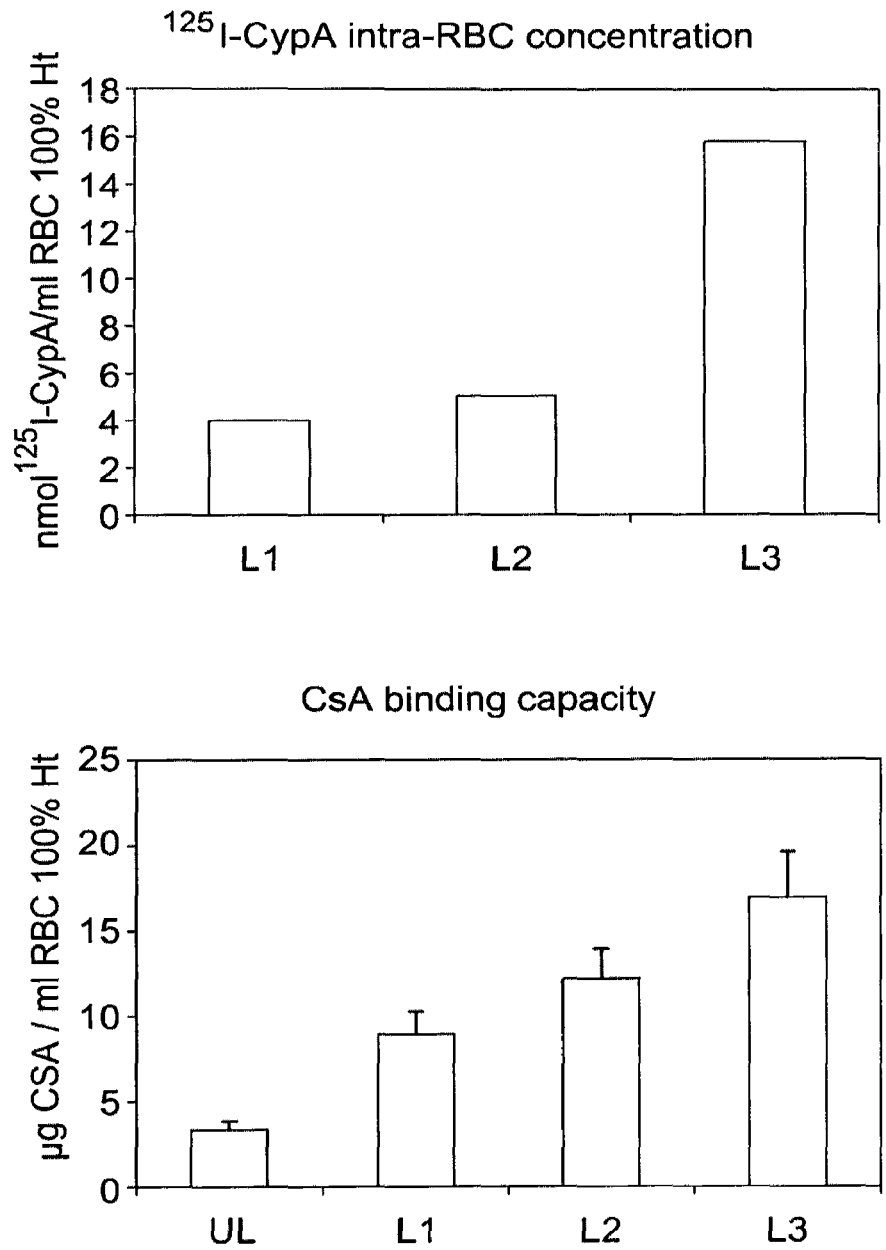

FIG. 11—$^{125}$I-CypA intra-erythrocytic concentration and CsA binding capacity of CypA-loaded RBC. Upper panel: $^{125}$I-CypA was loaded into human RBC and the recovered radioactivity used to estimate the amount of entrapped protein under the different loading conditions. Lower panel: In the histogram are represented the binding capacities for CsA observed for loaded RBC at 20, 40 and 80 µM CypA concentration compared with that found for un-loaded erythrocytes.

DETAILED DESCRIPTION OF THE INVENTION

Evaluation of the in vitro stability of FKBP12-loaded RBC showed that no differences exist between the survival curves of loaded erythrocytes compared with that of un-loaded cells, suggesting that the protein surplus does not decrease cell vitality. We have also shown that loaded erythrocytes have a strikingly higher binding capacity for the drug compared with native RBC.

Furthermore, our data proves that the amount of drug associated with red blood cells is closely dependent on the concentration of protein added to the RBC suspensions in the dialysis step. Preferably, the drug-protein binding is stoichiometric at a proportion of about 1:1, and this is thought to be reflected inside red blood cells. Thus, it has been shown that:

1) it is possible encapsulate a protein such as FKBP12 into human erythrocytes;

2) the encapsulation is dose-dependent; and 3) higher protein entrapment corresponds to a higher intra-erythrocytic drug concentration. Indeed, red blood cells loaded with increasing protein quantities (20, 40 and 80 µM) were able to bind a quantity of drug 4, 6 and 11 times greater than native cells.

A further advantage is that the processed RBCs of the present invention avoid premature hepatic metabolism and, by using autologous erythrocytes as a vehicle, anaphylactic reactions are avoided.

After processing to incorporate carrier protein and drug, the RBCs may be suspended in a suitable vehicle. This may be saline, but is preferably plasma, and may suitably be plasma from the patient, and may be plasma put to one side when isolating the RBCs from the patient. If the vehicle is not plasma, then it will be appreciated that care should be taken to avoid osmotic shock by using a physiological saline solution.

The RBC preparation may optionally contain other ingredients, such as an energy source, and preservatives, and may be stored in any manner suitable to store blood.

The amount of preparation used may typically be between 50 ml and 500 ml, and may be administered as often as advised by a physician. This may be once a day, once a week, once a month or any other interval, as appropriate.

A particularly preferred embodiment of the present invention provides an RBC with enhanced levels of FKBP12 (the 12-kDa FK506 Binding Protein, see below). There is further provided such an RBC wherein all, or a substantial proportion of, the FKBP12 is in the form of an association complex with FK506. This embodiment is further described below.

Tacrolimus (also known as FK506, Prograf) is a macrolide antibiotic produced and isolated from the actinomycete *Streptomyces tsukubaensis*, and has very high immunosuppressive activity. First approved in 1994 for the prevention of rejection in liver transplants, FK506 is now indicated in several countries as a primary immunosuppressive therapy in liver, kidney, pancreas, heart and lung transplantation or as rescue therapy in allograft rejections which are resistant to other immunosuppressive agents, or where such agents produce intolerable side effects [Tsunoda S M 2000, Ciancio G 1999, Plosker G L 2000].

Tacrolimus 3S-[3R*[E(1S*,3S*,4S*)],4S*,5R*,8S*,9E, 12R*,14R*,15S*,-16R*,18S*, 19S*,26aR*]]-5,6,8,11,12, 13,14,15,16,17,18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]oxaazacyclotricosine-1,7,20,21(4H,23H)-tetrone monohydrate, CAS number 104987-11-3), like Cyclosporin, belongs to the class of "calcineurin inhibitors", since its immunosuppressive activity depends on its ability to bind and inhibit the enzyme calcineurin, a serine/threonine calcium-dependent phosphatase. At the molecular level, the binding of the drug with phosphatase is mediated by a cytosolic protein belonging to the immunophillin family, the 12-kDa FK506 Binding Protein (FKBP12). In situ, FK506 binds FKBP12, and the resulting FK506-FKBP12 duplex forms a ternary complex with calcineurin, thereby inhibiting its activity. Enzyme inhibition results in the blocking of the dephosphorylation of NF-AT (Nuclear Factor of Activated T-cells), thereby impeding its translocation into the nucleus and the transcription of the IL-2 gene [Griffith J P 1995].

Macroscopically, the blocking of IL-2, and other pathways, by Tacrolimus results in a lack of activation and proliferation of T-cells, and in the inhibition of the cell-mediated immune response.

Despite its therapeutic efficacy, demonstrated by an in vitro potency 100 times greater than Cyclosporin and an in vivo reduction of tissue rejection incidence [Armenti V T 1998], FK506 possess a very narrow therapeutic window (5-20 ng/ml whole blood 10-12 hours post-dose) and frequently exhibits episodes of toxicity, including nephrotoxicity, neurotoxicity, glucose intolerance, etc. [Tsunoda S M 2000; Kershner R P, 1996]. Moreover, FK506 presents a high variability in pharmacokinetic profile between patients, and an extensive pre-systemic and systemic metabolism showing an oral bioavailability that ranges from 4 to 93% and a half-life in circulation between 3.5 and 40 hours [Undre N A 2003, Iwasaki K 2007]. The poor correlation of dose to blood concentration, and the low therapeutic index, make monitoring of Tacrolimus whole blood concentrations necessary in patients subjected to treatment with the drug (Therapeutic Drug Monitoring) [Shaw L M 1999]. Further, although endovenous infusion bypasses adsorption and bioavailability issues, this form of parenteral administration is often compromised by anaphylactic reactions induced by the vehicle (PEG-60 hydrogenated castor oil) utilised as emulsifier to stabilise Tacrolimus in aqueous solutions.

FK506 in blood is mainly associated with erythrocytes (about 85%) followed by plasma (14%) and lymphocytes (0.46%) [Chow F S 1997]. This high RBC fraction is due to the presence in erythrocytes of at least two types of immunophilins that bind the drug with very high affinity: FKBP12 (cited above), a 12-kDa cytosolic protein with peptidyl-prolyl cis-trans isomerase activity, and FKBP-13, a 13-kDa membrane associated protein with 43% amino acid identity with FKBP12 [Walensky L D 1998]. The binding capacity of RBC is calculated around 440 ng/ml of blood [Chow F S 1997].

FKBP 12 and its analogues are useful proteins for forming association complexes, and may also be used to complex other immunosuppressant drugs, such as rapamycin, for example.

The cyclophilins and their analogues are further examples of proteins that may also be used to complex immunosuppressants, especially cyclosporin. Cyclosporin A (CsA) is a lipophilic cyclic polypeptide, produced by the fungus *Tolypocladium inflatum*, that belongs to the class of "Calcineurin inhibitors" immunosuppressants. CsA, like Tacrolimus, inhibits the activation of the calcium/calmodulin-activated phosphatase calcineurin via complex formation with cyclophilin and thereby prevents the translocation of the transcription factor "Nuclear Factor of Activated T cells" (NF-AT) [Dunn C J 2001]. Since it was introduced in the first 1980s, Cyclosporine A has improved the outcome of solid organ transplantation. Unfortunately, CsA is characterized by high intra- and inter-patient pharmacokinetic variability and poor bioavailability. The bioavailability of CsA may be affected by several factors including time post-surgery, concomitant therapy, change in gastrointestinal function, and pharmaceutical preparation [Faulds D 1993, Pollard S 2003] as well as by genetic polymorphisms in the MDR1 gene or CYP3A4/CYP3A5 genes [Cattaneo D 2004]. Furthermore, the tolerability profile of cyclosporin is characterised by a number of potentially serious adverse effects that are related to exposure, including acute or chronic nephrotoxicity, hypertension and neurotoxicity. The main dose-limiting adverse effect of cyclosporin is nephrotoxicity, which usually presents as a reversible decrease in glomerular filtration rate [Naesens M 2009].

At whole blood concentration of 50-1000 ng/ml, more than 70% of CsA is associated to erythrocytes; cytosolic CsA is bound to the erythrocyte peptidil-prolil cis-trans isomerase Cyclophilin A [Foxwell B M 1988]. The total RBC binding capacity for CsA amounted to $43 \times 10^{-5}$ nmol per $10^6$ RBC [Foxwell B M 1988, Reichel C 1994].

The following example relates with the possibility of increasing the amount of CsA associated with RBC by increasing the cytosolic concentration of the Cyclophilin A (CypA) immunophilin.

It is particularly preferred that FKBP12 (or its analogues) is paired with FK506, or Cyclophillin is paired with CsA. However, FKBP12 (or its analogues) can be also paired with rapamycin. Therefore, FKBP12 may bind (and transport once entrapped into red blood cells) both tacrolimus (FK506) and rapamycin.

By analogues is meant any functional variant having the same or similar properties allowing it to function in the same way as the named molecule (be it the present drug or the present protein) in the present invention. The same applies to derivatives. For example, analogues of FKBP12 (also known as FKBP1A) include FKBP25, FKBP51 and FKBP52; and analogues of Cyclophilin A include Cyclophilin A. Analogues of rapamycin are known in the art as "rapalogs" and include fluorinated rapamycin analogues (Chembiochem. 2010 Mar. 22; 11(5):698-702). Analogues of Cyclosporine include Cyclosporine A, aureobasidin A, PKF-211-811-NX5 (NIM811) and sanglifehrin A (Arterioscier Thromb Vasc Biol. 2010 March; 30(3):419-25) and other analogues disclosed in Biochemical and Biophysical Research Communications, Volume 363, Issue 4, 30 Nov. 2007, Pages 1013-1019, incorporated herein by reference.

For instance, rapamycin has been shown to associate with immunophillin FKBP12 and FKBP 25, both binding rapamycin with high affinity (Biochemistry. 1992 Mar. 3; 31(8): 2427-34. A rapamycin-selective 25-kDa immunophilin. Galat A, Lane W S, Standaert R F, Schreiber S L.)

The protein, for instance FKBP12, may be encapsulated into (preferably human) erythrocytes by means of a procedure of hypotonic dialysis, isotonic resealing and "reannealing." It is particularly preferred that this method is as previously described in EP 0 882 448 A1 or as described in greater detail in the present Examples. In brief, it is preferred that human red blood cells were obtained from fresh blood collected and washed to remove leukocytes and platelets. Recovered RBC are then re-suspended, for instance at 70% haematocrit, in physiologic solution. The suspension may then be aliquoted and the protein added at increasing concentrations. Each erythrocyte suspension can then be dialysed in dialysis tubes and RBC suspensions collected and allowed to equilibrate. Erythrocyte resealing may be obtained by incubation of cells with relatively small volumes (for instance only 0.1 volumes) of hypertonic solution under known resealing conditions (for instance at 3000 mOsm containing inosine 100 mM, ATP 20 mM, glucose 10 mM, sodium pyruvate 100 mM, MgCl2 4 mM, NaCl 190 mM, KCl 1666 mM and NaH2PO4 33 mM (pH 7.4)).

The resealed RBC may then be incubated at body temperature in the presence of the hypertonic solution in order to permit the re-annealing of the membrane segments and increase final cell recovery. Finally, loaded erythrocytes were washed at least once in physiologic buffer to remove the un-loaded FKBP12 fraction from the external medium. RBC corpuscolar indices MCV, Mean Corpuscular Volume, MCH, Mean Corpuscular Haemoglobin and MCHC, Mean Corpuscular Haemoglobin Concentration) can then be evaluated for both loaded and un-loaded cells at the end of the procedure. Further details are provided in the Examples.

The present invention increases the amount of drug carried by erythrocytes in order to use them as a slow delivery system for drugs, especially immunosuppressants, particularly Tacrolimus, rapamycin and/or cyclosporine, and analogues or derivatives, and distribute low doses of the same in circulation. Administration through autologous erythrocytes ensures a safe and non-immunogenic vehicle for the drug, protects from premature hepatic metabolism, and reduces side effects by providing low and constant doses of drug, without producing peaks in plasma levels.

Recombinant proteins are included within the scope of the term "protein" herein. In particular, recombinant FKBP12 (rFKBP12) is preferred as the protein.

The present invention will be further illustrated in the following, non-limiting Examples. All references are hereby incorporated herein by reference to the extent that they do not conflict with the present invention.

EXAMPLES

Materials and Methods

Figure 1:
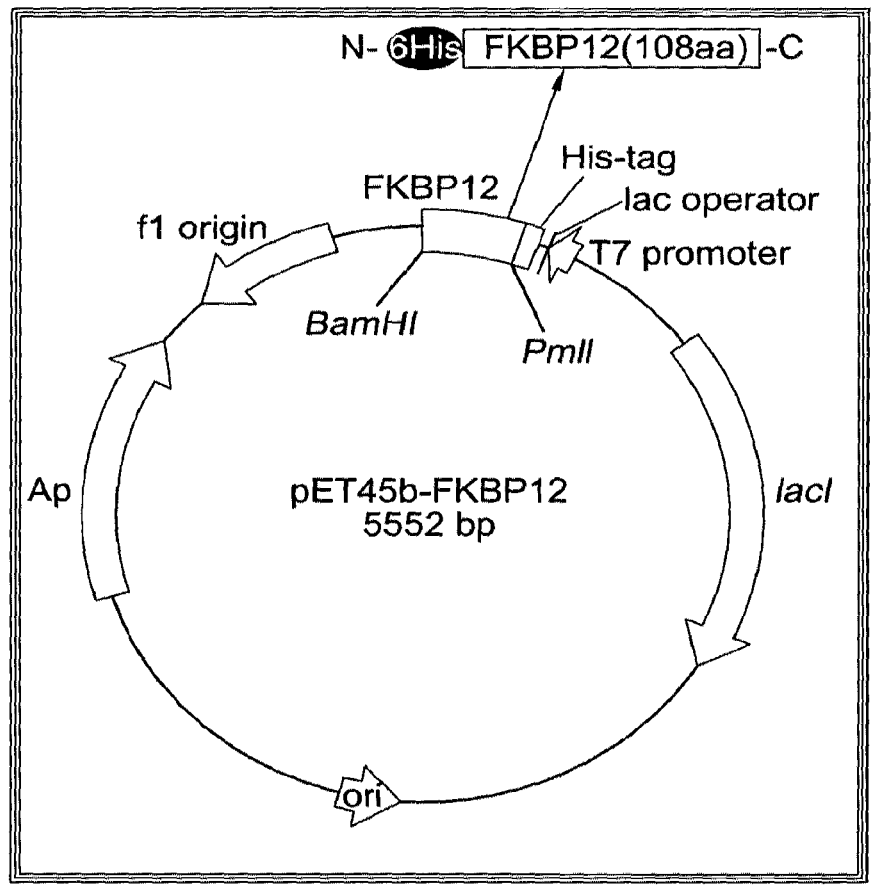
FIG. 1—pET-45b(+)—FKBP12 construct. The cDNA coding for the full length FKBP12 was inserted in the pET-45b(+) vector downstream of the poly(histidine) tag coding sequence. The transcription of DNA insert cloned under the T7 promoter will originate a recombinant form of human FKBP12 with histidine tag at the N-terminal domain.

Manufacturing of a Recombinant Form of Human FKBP12:

total mRNA was extracted from U937 cells and amplified by polymerase chain reaction (PCR) using an oligo-dT as non-specific primer, cDNA was then obtained by retro-transcription. Successively, the cDNA segment coding for the FKBP12 gene (GenBank accession number NM_000801) was amplified by PCR with 5'-TCCGCCCACGTGATGG-GAGTGCAGGTGGAAAC-3' (SEQ ID NO: 1) as forward primer and 5'-GAGGCCAGGATCCTCATTCCAGTTTTA-GAAGC-3' (SEQ ID NO: 2) as reverse primer. The resulting PCR product was verified by sequencing in both directions with a capillary sequencer (PE 310 Perkin Elmer). FKBP12-cDNA was finally purified through MiniElute PCR Purification Kit (Qiagen), digested with BamHI and Finn and ligated into a pET-45b(+) vector (Novagen) similarly digested. The FKBP12 gene was inserted into the expression vector downstream of the poly(histidine) tag coding sequence (FIG. 1) so that the transcription and translation of the plasmid will produce an N-terminal His-tagged FKBP12 (6His-FKBP12, SEQ ID NO: 3):

```
ATGGCACATCACCACCACCATCACGTGATGGGAGTGCAGGTGGAAACCA

TCTCCCCAGGAGACGGGCGCACCTTCCCCAAGCGCGGCCAGACCTGCGT

GGTGCACTACACCGGGATGCTTGAAGATGGAAAGAAATTTGATTCCTCC

CGGGACAGAAACAAGCCCTTTAAGTTTATGCTAGGCAAGCAGGAGGTGA

TCCGAGGCTGGGAAGAAGGGGTTGCCCAGATGAGTGTGGGTCAGAGAGC

CAAACTGACTATATCTCCAGATTATGCCTATGGTGCCACTGGGCACCCA

GGCATCATCCCACCACATGCCACTCTCGTCTTCGATGTGGAGCTTCTAA

AACTGGAATGA
```

E. coli BL21(DE3) competent cells (Stratagene) were transformed by the pET45b-FKBP12 obtained construct. The cells were next grown in Luria-Bertani (LB) medium (Bacto-Tryptone 10 g/l, Bacto-yeast extract 5 g/l, NaCl 10 μm at pH 7.0) containing ampicillin (50 μg/ml) at 37° C. under shaking until culture optical density at 600 nm reached 0.6-0.7. Overexpression of recombinant FKBP12 was then induced by addition to the culture broth of Isopropyl-beta-D-TioGalattoPiranoside (IPTG) 1 mM and growth for a further 2 hours at 37° C. under shaking. Induced BL21(DE3) were pelleted and lysed by homogenisation performed in lysis buffer (phosphate buffer 20 mM pH 7.4, NaCl 0.5 M, imidazole 10 mM, β-mercaptoethanol 3 mM and PMSF (phenylmethanesulphonylfluoride) 0.1 mM) with Emulsifier-05 (Avestin Inc., Ottawa, ON, Canada). 6His-FKBP12 was purified to homogeneity through a single step Ni-Affinity chromatography performed on AKTA Purifier (Amersham Pharmacia Biotech). After centrifugation at 15000 rpm for 30 minutes, the homogenate was loaded onto a Ni Sepharose High Performance packed column pre-equilibrated with phosphate buffer 20 mM pH 7.4, NaCl 0.5 M, Imidazole 10 mM and MSH 3 mM. The column was washed extensively to remove unbound proteins and elution of bound proteins was carried out by Imidazole gradient from 10 to 250 mM in the same buffer. Eluted fractions were analysed by SDS-page and the ones more pure containing 6His-FKBP12 were re-united and dialysed against 2 liters of storage buffer (Hepes 50 mM pH 8.0, NaCl 150 mM, EDTA 0.5 mM, sodium azide 1 mM). Final purity of recombinant FKBP12 was verified by electrophoresis on 15% acrylamide gel and Coomassie Blue staining and the identity of the purified protein attested by immunoblotting using a mouse polyclonal anti-FKBP12 (Abnova, Taipei city, Taiwan).

Preliminary Binding Studies rFKBP12-FK506:

the ability of 6His-FKBP12 to bind the FK506 ligand was assessed by a slightly modified Dot Blot analysis. Briefly, 6His-FKBP12 in native conditions was dot-blotted onto a 0.2 μm nitrocellulose membrane at increasing concentrations (2.5, 5, 10 μg/well). Successively, the membrane was subjected to a single incubation step with a solution of Tacrolimus-horseradish peroxidase conjugate (PRO-Trac™ II Tacrolimus 5× Conjugate, DiaSorin, Stillwater, Minn., USA) to allow FKBP12-Tacrolimus binding. After washing with Tris Saline Buffer (TBS) with 0.05% Tween20, the signal was revealed by ECL system (Amersham Pharmacia Biotech).

Loading of Recombinant FKBP12 into Human Erythrocytes:

recombinant FKBP12 was encapsulated into human erythrocytes by means of a procedure of hypotonic dialysis, isotonic resealing and "reannealing" as previously described [Magnani M 1989]. In particular, human red blood cells were obtained from fresh blood collected in heparin from healthy donors and washed with physiologic solution containing Hepes 10 mM (pH 7.4), NaCl 154 mM and Glucose 5 mM to remove leukocytes and platelets. Recovered RBC were re-suspended at 70% haematocrit in physiologic solution, the suspension aliquoted in 3 tubes and rFKBP12 added at increasing concentrations (20, 40, 80 μM/tube). Each erythrocyte suspension was dialysed in dialysis tube with 3.5 kDa cut-off for 90 minutes at 4° C. against 50 volumes of hypotonic solution 60 mOsm containing NaH2PO4 10 mM, NaHCO3 10 mM pH 7.4, glucose 20 mM, GSH 3 mM and ATP 2 mM. At the end of the dialysis step, RBC suspensions were collected and allowed to equilibrate at 37° C. for 5 minutes under gentle stirring. Erythrocyte resealing was obtained by incubation of cells with 0.1 volumes of hypertonic solution at 3000 mOsm containing inosine 100 mM, ATP 20 mM, glucose 10 mM, sodium pyruvate 100 mM, MgCl2 4 mM, NaCl 190 mM, KCl 1666 mM and NaH2PO4 33 mM (pH 7.4). Resealed RBC were incubated for 25 minutes at 37° C. in the presence of the hypertonic solution in order to permit the re-annealing of the membrane segments and increase final cell recovery. Finally, loaded erythrocytes were washed 2 times in physiologic buffer to remove the un-loaded FKBP12 fraction from the external medium. RBC corpuscolar indices MCV, Mean Corpuscular Volume, MCH, Mean Corpuscular Haemoglobin and MCHC, Mean Corpuscular Haemoglobin Concentration) were evaluated for both loaded and un-loaded cells at the end of the procedure.

In Vitro Stability of FKBP12-Loaded Erythrocytes:

the in vitro stability of FKBP12-loaded erythrocytes was assessed until 6 days after loading procedure. Loaded RBC were re-suspended at 0.5% haematocrit in RPMI-1640 supplemented with 10% FBS, 50 µg/ml streptomycin and 50 units/ml penicillin and incubated in a humidified atmosphere at 37° C. with 5% $CO_2$. At times 0, 1, 2, 3 and 6 days the percentage of survived cells was calculated. In detail, the suspensions were collected, centrifuged and the pelleted cells re-suspended in a fixed quantity of Hepes solution. Volume and haematocrit of RBC suspensions were evaluated and the cell survival calculated for all samples. In parallel, MCV, MCH and MCHC were evaluated. Unloaded erythrocytes, subjected to the same loading process but without adding of FKBP12 during the dialysis step, were used as control for cell survival and valuation of red blood cell parameters.

Evaluation of the Tacrolimus Binding Capacity Acquired by FKBP12-Loaded Erythrocytes:

FKBP12-loaded RBC obtained at the end of the loading procedure were re-suspended in Hepes solution at physiologic haematocrit (40%) and Prograf 5 mg/ml Concentrated Injection was then added at 20 µg/ml RBC suspension to test the new RBC binding capacity for the drug (FK506 binding capacity for native RBC was calculated 0.4 µg/ml RBC 40% Ht). Cells were allowed to incubate for 1 hour at 37° C. in order to permit drug equilibration between intracellular and extracellular compartments. Erythrocytes were then washed with saline (pH 7.4) to remove un-bound Tacrolimus from the external medium. Native RBC obtained from fresh blood collected in heparin from healthy donors were used as control during the experiment.

The amount of Tacrolimus associated with FKBP12-loaded and native erythrocytes was evaluated through a Dimension RXL analyzer (RXL Dimension, Siemens, ex-Dade Behring). The Dimension analyzer measures FK506 levels in whole blood samples by an Antibody Conjugated Magnetic Immuno-Assay (ACMIA). The assay is performed using a specific Flex reagent cartridge. The TACR Flex cartridge contains a pre-treatment reagent, β-galactosidase-FK506 antibody conjugate, FK506 immobilized on chromium dioxide particles, chlorophenol red β-d-galactopyranoside substrate (CPRG) and diluent to hydrate the tablets. Whole blood (200 µL) from an EDTA collection tube, mixed on an inverter, is first added to a sample cup by the operator. The Dimension uses a sonicating probe to mix the sample, lyses the blood cells using a saponin-based buffer and sonication, and then adds a FK506 antibody/β-galactosidase conjugate. The FK506 present in the sample is bound by the FK506 antibody-conjugated reagent. Magnetic particles coated with FK506 are added to bind free antibody-enzyme conjugate. The reaction mixture is then separated magnetically. Following separation, the supernatant containing the FK506-antibody-enzyme complex is transferred to another cuvette and mixed with the substrate. β-Galactosidase catalyzes the hydrolysis of CPRG to produce chlorophenol red (CPR) that absorbs light maximally at 577 nm.

Loading of $I^{125}$-FKBP12 into Human RBC:

in order to demonstrate that the higher amount of FK506 bound to engineered FKBP12-RBC is due to the presence of increasing concentrations of protein, a loading procedure was performed with radiolabelled-FKBP12. Briefly, $^{125}I$-FKBP12 was obtained through iodination of Tyr residue by means of chemical activation of sodium iodine (Perkin Elmer, Waltham, USA) with chloramine T (Sigma Aldrich, St. Louis, USA). The obtained $I^{125}$-FKBP12 (specific activity of 3045 cpm/µg) has been encapsulated into human erythrocytes through hypotonic dialysis and isotonic resealing performed in the same conditions as previously reported (20, 40 and 80 µM protein/ml RBC). Loaded cells were subjected to solubilisation and haemoglobin oxidation with, respectively, hydrogen peroxide and Solvable (Perkin Elmer, Waltham, USA) as detailed in Perkin Elmer Protocol for Sample Preparation and Counting for whole blood samples. RBC lysates were then added with Emulsifier Scintillator Plus cocktail (Packard) and radioactivity measured by Liquid Scintillation Counter (Packard).

Results

Figure 2:
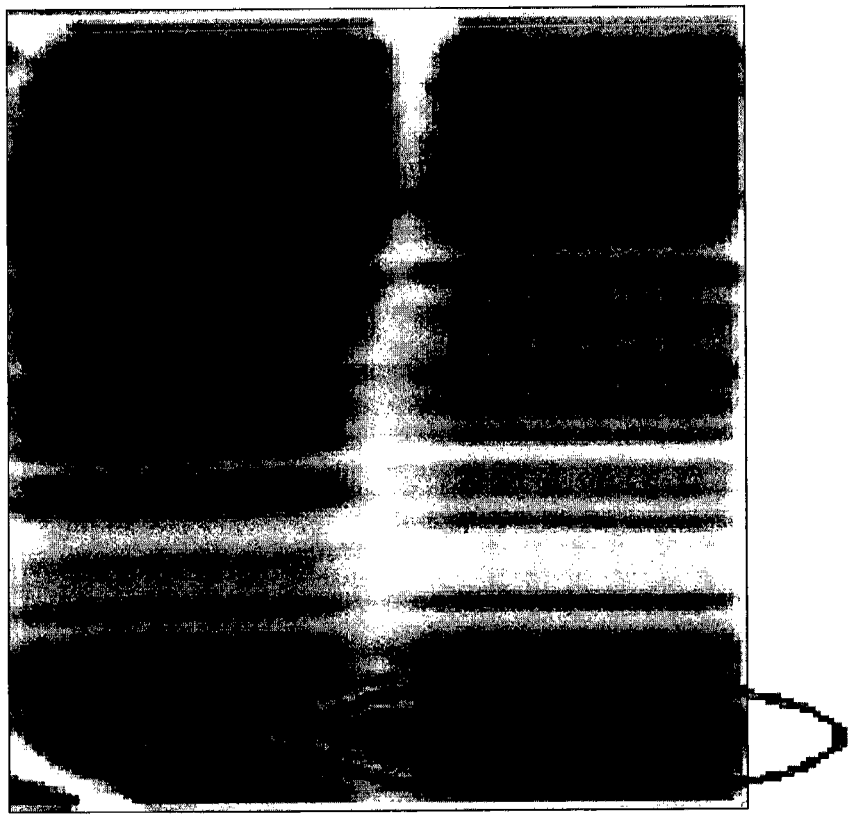
FIG. 2—SDS-page of BL21(DE3) homogenates. Lane 1: not induced BL21(DE3), lane 2: BL21(DE3) induced with IPTG. Total protein extracts (30 μg) obtained from homogenized BL21(DE3) cells were separated on 15% SDS-polyacrylamide gel.
Figure 3:
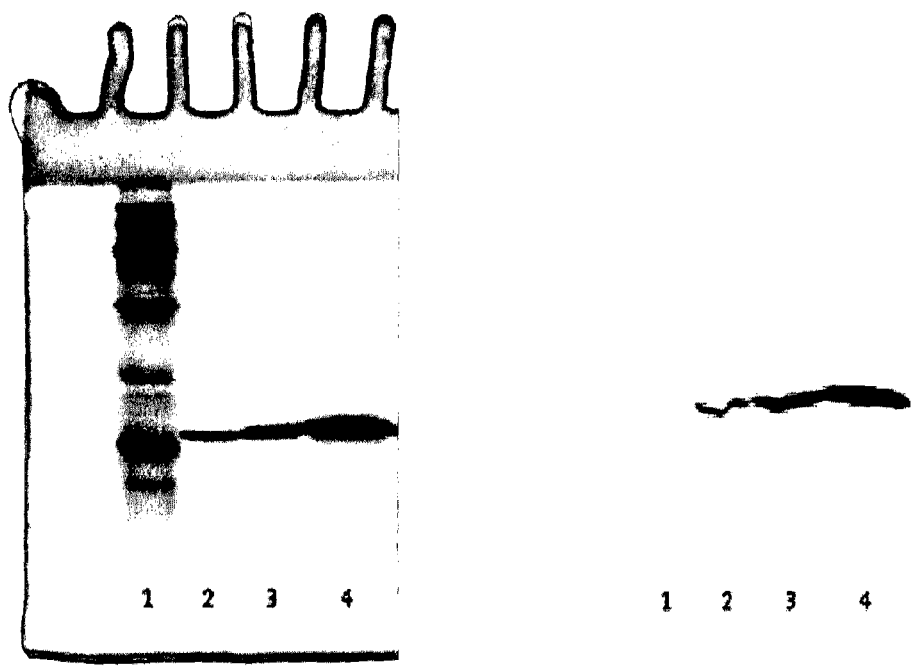
FIG. 3—Characterization of purified FKBP12 a) SDS-PAGE b) immunoblotting. Lane 1: Low Molecular Weight standards, lane 2: FKBP12. 1.0, 2.5 and 5.0 μg of purified FKBP12 were subjected to electrophoretic run on 15% SDS-page followed by Coomassie Blue staining and densitometric assay to verify the protein molecular weight and purity level.

Manufacturing of a Recombinant Form of Human FKBP12:

the recombinant His-tagged FKBP12 was effectively expressed in BL21(DE3) E. Coli strain as demonstrated by the SDS-page of bacterial homogenate (FIG. 2). The Figure represents the SDS-PAGE of non-induced BL21(DE3) homogenate (lane 1) used as control and induced BL21(DE3) homogenate (lane 2). After Coomassie Blue stain, a protein band can clearly be seen in lane 2, which is absent in the control. Moreover, thanks to the high affinity of histidine tag for nickel ions, 6His-FKBP12 by a single step of affinity chromatography was isolated from the protein pool in the bacterial homogenate. The purified FKBP12 was finally analysed by polyacrylamide gel electrophoresis and densitometric assay to verify molecular weight and purity grade of the obtained protein. By western blotting the protein bands were next revealed with a polyclonal antibody against FKBP12 enlightening that the purified protein is effectively the 12-kDa FK506 Binding Protein. In FIG. 3 the electrophoretic run of final FKBP12 and the immunoblot are reported; both indicates the presence of a single band of 13-14 kDa and a purity level higher than 99%.

Figure 4:
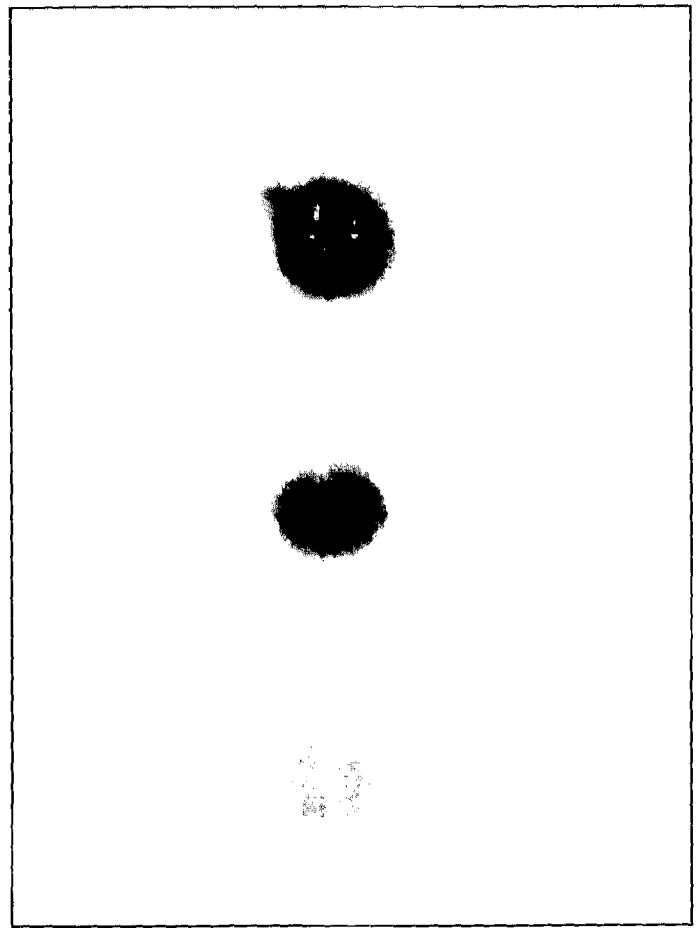
FIG. 4—Dot blot analysis of rFKBP12-FK506 binding. From the top to the bottom: FKBP12 10, 5 e 2.5 µg/well. Different amounts of FKBP12 were loaded on a 15% polyacrylamide gel, blotted on 0.2 µm pore-size nitrocellulose membrane and subjected to Dot Blot analysis as described in the Materials and Methods section.

Preliminary Binding Studies rFKBP12-FK506:

the ability of 6His-FKBP12 to bind the FK506 ligand was verified. In FIG. 4, the exposition on X-ray film of the nitrocellulose membrane after ECL reaction shows that the intensity of blots signal results directly proportional to the amount of spotted protein, thus demonstrating that recombinant FKBP12 is able to bind Tacrolimus in a specific and dose-dependent manner.

Figure 5:
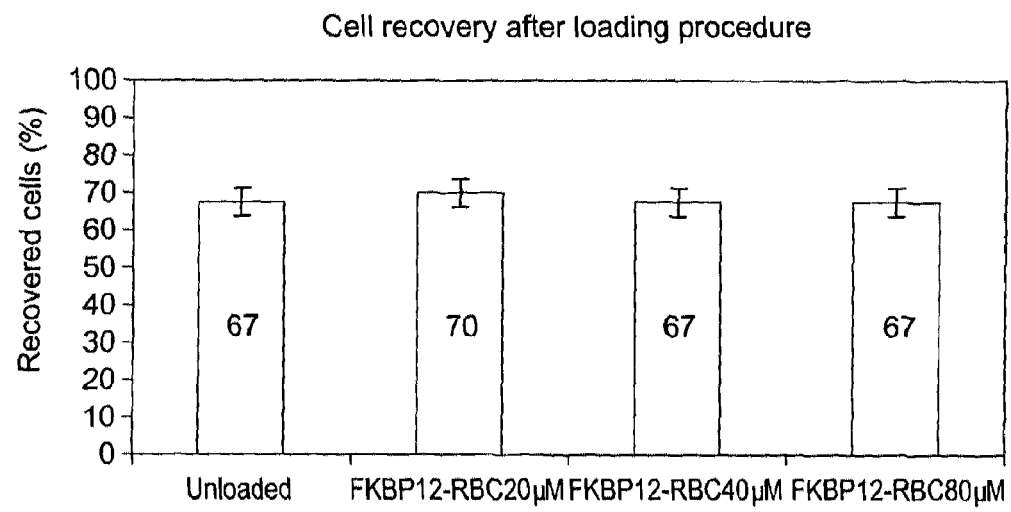
FIG. 5—Cell recovery. The percentage of cell recovery obtained at the end of the loading procedure were calculated for FKBP 12-loaded RBC (20, 40 and 80 µM) and un-loaded RBC respectively to not treated cells added at the beginning of the procedure.
Figure 6:
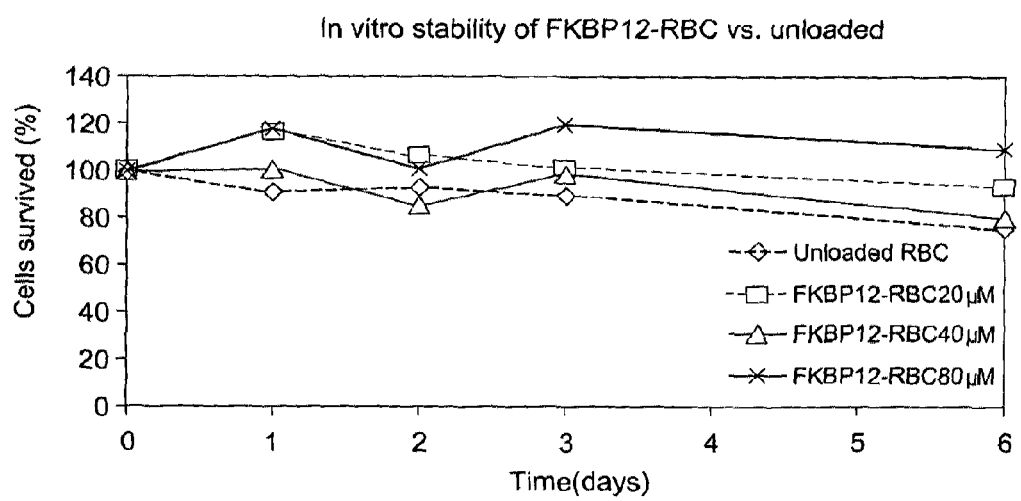
FIG. 6—Stability of loaded cells. The cells subjected to loading procedure (Loaded and Un-Loaded RBC) were incubated until 6 days before the treatment and the survival curves estimated for each sample.

Loading of Recombinant FKBP12 into Human Erythrocytes and Stability of FKBP12-Loaded RBC:

At the end of the loading procedure an optimal cell recovery was obtained for all conditions of incubation with FKBP12. The percentage of recovered cells resulted 70, 67 and 67% for dialysed RBC incubated with 20, 40 and 80 µM FKBP12 concentration respectively, fully comparable with that calculated for un-loaded erythrocytes (FIG. 5). Moreover, the erythrocytic indices have been investigated for un-loaded and loaded cells, revealing that FKBP12-RBC possess MCV, MCH and MCHC values completely comparable to un-loaded erythrocytes (Table 1); by comparing treated RBC with native cells, it can be highlighted only a little decrease in mean cellular volume but the haemoglobin concentrations are in the variability range. The cell survival calculated for FKBP12-loaded RBC at 1, 2, 3, and 6 days is equal or higher in all loading conditions compared with un-loaded erythrocytes, as shown in FIG. 6. The differences observed in the percentage of survival cannot be attributed to the amount of protein added to cell suspensions in the dialysis tube. In Table 2, the MCV, MCH and MCHC values are summarised. Once again differences cannot be attributed between erythrocytes loaded with FKBP12 and controls at the reported times. Furthermore, the values obtained among loaded RBC do not present significant variations for increasing FKBP12 concentrations. Finally, small reductions in haemoglobin content and haemoglobin concentration were noticed in all groups at the sixth day, probably due to the beginning of haemolysis consequent to the experimental procedure.

Figure 7:
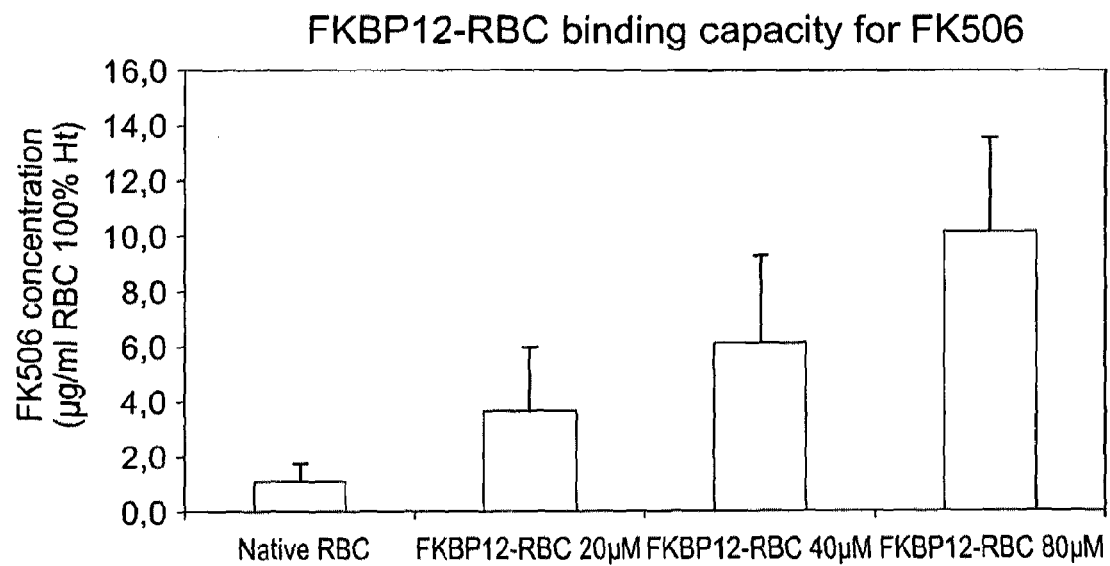
FIG. 7—FKBP12-loaded RBC binding capacity for Tacrolimus. The graphic displays the binding capacity for Tacrolimus calculated for FKBP12-loaded RBC at 20, 40 and 80 µM protein concentration compared with that calculated for native erythrocytes.

Evaluation of Tacrolimus Binding Capacity Acquired by FKBP12-Loaded Erythrocytes:

Tacrolimus levels were quantified by means of the immunoenzymatic assay on the pellets of FKBP12-loaded and native RBC. The results, reported in FIG. 7, demonstrate that FKBP12-loaded erythrocytes were able to bind higher amounts of drug compared with native cells. Furthermore, the graphic highlights how the quantity of FK506 associated with loaded red blood cells increases proportionally to the FKBP12 concentration added during the dialysis step. In fact, erythrocytes dialysed with FKBP12 concentrated 20, 40 and 80 µM were able to bind a drug amount equivalent to $3.5\pm2.0$, $6.0\pm2.6$ e $11.4\pm3.8$ µg/ml RBC at 100% haematocrit respectively, exactly 4, 6 and 11 times greater than native RBC ($1.0\pm0.4$ µg/ml RBC 100% Ht).

Figure 8:
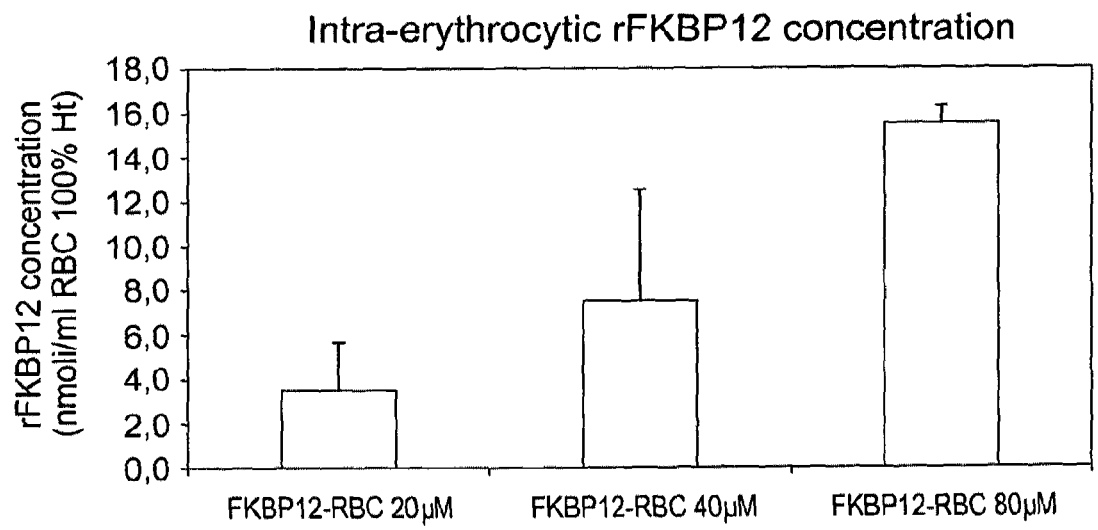
FIG. 8—Recombinant FKBP12 concentration into engineered RBC. rFKBP12 concentrations achieved into human erythrocytes have been evaluated by carrying on loading procedures with a radio-labelled FKBP12 specie performed in the same loading conditions previously reported (20, 40 and 80 µM protein versus ml RBC).

Loading of $I^{125}$-FKBP12 into Human RBC:

$^{125}$I-FKBP12 was loaded into human erythrocytes in order to demonstrate that the recombinant protein can be effectively entrapped thanks to the loading procedure. By dialyzing human RBC with the radio-labelled protein at the concentration of 20, 40 e 80 µM as described in the Methods section, an increasing intra-erythrocytic FKBP12 concentration could be obtained. In particular, in FKBP12-loaded RBC were achieved $3.5\pm2.5$, $7.4\pm5.4$ and $15.4\pm0.6$ nmoles per milliliter of packed RBC, respectively for cells dialyzed against 20, 40 e 80 µM of protein (FIG. 8).

Discussion

The transcription and translation of the construct produce a protein with the sequence Met-Ala-6His-Val prior to the 108 amino acids that compose the native protein. The 9 additional amino acids provide an increase in the final protein molecular weight of at least 1.3 kDa (from 12 kDa to 13-14 kDa) as demonstrated by the SDS-page analysis conducted in the experimental section. However, the presence of the histidine tag makes the purification process extremely simple and rapid since it only requires an affinity chromatography step. Moreover, the single step purification protocol provides high yield and purity, with about 50 mg obtained from 1 L of E. coli culture more than 99% purity. Finally, the presence of the poly(histidine) tag does not compromise the folding and the functionality of the protein, as demonstrated in the Dot Blot binding assay. This evidence is also reported in literature, although the authors produced a recombinant FKBP12 with longer "His-based" N-terminal tags. [Wear M A 2006].

Concerning FKBP12 loading in human erythrocytes by means of the hypotonic dialysis method, the protein was added directly in the dialysis tube because the entry of high molecular weight substances seems to be favoured while reaching osmotic equilibrium. At the three tested concentrations (20, 40 and 80 µM), FKBP12 does not appear haemolytic and cell recovery was optimal in all conditions, revealing that it was completely independent from the presence and the concentration of FKBP12.

Evaluation of the in vitro stability of FKBP12-loaded RBC showed that no differences exist between the survival curves of loaded erythrocytes compared with that of un-loaded cells, suggesting that the protein surplus does not decrease cell vitality. Finally, loaded erythrocytes were investigated for their ability to bind Tacrolimus. A strikingly higher binding capacity for FK506 for FKBP12-loaded RBC compared with native RBC (utilized as control during the experiments) was demonstrated. In addition, it was proved that the amount of drug associated with red blood cells is closely dependent on the concentration of protein added to the RBC suspensions in the dialysis step. Since drug-protein binding is stoichiometric at the proportion 1:1, it seems likely that the FK506 concentration is in direct relation to the FKBP12 concentration inside red blood cells. Moreover, comparing the expected drug concentrations in erythrocytes derived from the experiments employing radio-labelled FKBP12 (Table 3) with those measured in the FK506 binding capacity tests, very similar intra-erythrocytic Tacrolimus concentrations were found.

Thus, it has been shown that:
1) it is possible encapsulate FKBP12 into human erythrocytes;
2) the encapsulation is dose-dependent; and
3) higher FKBP12 entrapment corresponds to a higher intra-erythrocytic FK506 concentration; indeed, red blood cells loaded with increasing FKBP12 quantities (20, 40 and 80 µM) were able to bind a quantity of drug 4, 6 and 11 times greater than native cells.

The processed RBCs of the present invention avoid premature hepatic metabolism and, by using autologous erythrocytes as a vehicle, anaphylactic reactions are avoided.

REFERENCES

1. Armenti V T, Moritz M J, Davison J M. Drug safety issues in pregnancy following transplantation and immunosuppression: effects and outcomes. Drug Saf. 1998 September; 19(3):219-32.
2. Chow F S, Piekoszewski W, Jusko W J. Effect of haematocrit and albumin concentration on hepatic clearance of tacrolimus (FK506) during rabbit liver perfusion. Drug Metab Dispos. 1997 May; 25(5):610-6.
3. Ciancio G, Burke G W, Roth D, Miller J. Tacrolimus and mycophenolate mofetil regimens in transplantation: benefits and pitfalls. Biodruga 1999 June; 1(6):395-407.
4. Flower R. Erythrocyte Movement in the Capillaries. Macula Meeting 16-17 January 2009 in New York University School of Medicine, New York.
5. Griffith J P, Kim J L, Kim E E, Sintchak M D, Thomson J A, Fitzgibbon M J, Fleming M A, Caron P R, Hsiao K, Navia M A. X-ray structure of calcineurin inhibited by the immunophilin-immunosuppressant FKBP12-FK506 complex. Cell. 1995 Aug. 11; 82(3):507-22.
6. Iwasaki K. Metabolism of tacrolimus (FK506) and recent topics in clinical pharmacokinetics. Drug Metab Pharmacokinet. 2007 October; 22(5):328-35. Review.
7. Kershner R P, Fitzsimmons W E. Relationship of FK506 whole blood concentrations and efficacy and toxicity after liver and kidney transplantation. Transplantation 1996; 62:920-6.
8. Magnani M, Rossi L, Bianchi M, Serafini G, Zocchi E, Laguerre M, Ropars C. Improved stability of 2,3-bisphpsphoglycerate during storage of hexokinase-overloaded erythrocytes. Biotechnol Appl Biochem 1989; 11:439-44.
9. Plosker G L, Foster R H. Tacrolimus: a farther update of its pharmacology and therapeutic use in the management of organ transplantation. Drugs 2000 February; 59(2):323-89.
10. Shaw L M, Holt D W, Keown P, Venkataramanan R, Yatscoff R W. Current opinions on therapeutic drug monitoring of immunosuppressive drugs. Clin Ther. 1999 October; 21(10):1632-52; discussion 1631.

11. Tsunoda S M, Aweeka F T. Drug concentration monitoring of immunosuppressive agent: focus on tacrolimus, mycophenolate mofetil and sirolimus. Biodrugs, 2000 December; 14(6):355-69.
12. Undre N A. Pharmacokinetics of tacrolimus-based combination therapies. Nephrol Dial Transplant. 2003 May; 18 Suppl 1:i12-5. Review.
13. Walensky L D, Gascard P, Fields M E, Blackshaw S, Conboy J G, Mohandas N, Snyder S H. The 13-kD FK506 binding protein, FKBP13, interacts with a novel homologue of the erythrocyte membrane cytoskeletal protein 4.1. J. Cell Biol. 1998 Apr. 6; 141(1):143-53.
14. Wear M A, Patterson A, Walkinshaw M D. A kinetically trapped intermediate of FK506 binding protein forms in vitro: chaperone machinery dominates protein folding in vivo. Protein Expr Purif. 2007 January; 51(1):80-95. Epub 2006 Jun. 28.

TABLE 1

Mean Corpuscular Volume (MCV), Mean Corpuscular Haemoglobin (MCH) and Mean Corpuscular Haemoglobin Concentration (MCHC) of FKBP12-loaded RBC vs. un-loaded and native RBC.

|  | MCV (fl) | MCH (pg) | MCHC (g/dl) |
|---|---|---|---|
| Reference values | 83-97 | 27-32 | 32-36 |
| Native RBC | 89 ± 1.6 | 29.6 ± 0.6 | 33.2 ± 0.4 |
| Un-loaded RBC | 78 ± 2.2 | 24.9 ± 0.9 | 31.9 ± 0.9 |
| FKBP12-RBC 20 µM | 78 ± 1.3 | 24.5 ± 0.6 | 31.3 ± 0.6 |
| FKBP12-RBC 40 µM | 78 ± 2.9 | 24.6 ± 0.7 | 31.4 ± 1.0 |
| FKBP12-RBC 80 µM | 79 ± 1.1 | 24.8 ± 0.3 | 31.3 ± 0.7 |

The results showed in the table above are the arithmetical means and the standard deviations of five loading experiments.

TABLE 2

MCV, MCH and MCHC values at 6 days for FKBP12-loaded vs. UL RBC

| Times (days) | MCV (fl) | MCH (pg) | MCHC (g/dl) | MCV (fl) | MCH (pg) | MCHC (g/dl) |
|---|---|---|---|---|---|---|
|  | Unloaded RBC | | | FKBP12-RBC 20 µM | | |
| 0 | 73 | 28.2 | 38.3 | 74 | 28.7 | 38.6 |
| 1 | 74 | 28.3 | 38.2 | 75 | 29.1 | 38.9 |
| 2 | 74 | 28.4 | 38.4 | 74 | 28.4 | 38.3 |
| 3 | 73 | 28.2 | 38.8 | 74 | 28.5. | 38.5 |
| 6 | 72 | 23.8 | 33.2 | 73 | 26.3 | 35.8 |
| Mean | 73.2 | 27.4 | 37.4 | 74.0 | 28.2 | 38.0 |
| St. Dev. | 0.8 | 2.0 | 2.3 | 0.7 | 1.1 | 1.3 |
|  | FKBP12-RBC 40 µM | | | FKBP12-RBC 80 µM | | |
| 0 | 74 | 28.8 | 38.9 | 73 | 28.3 | 38.4 |
| 1 | 75 | 29.6 | 39.7 | 74 | 28.6 | 38.4 |
| 2 | 74 | 28.4 | 38.4 | 73 | 29.3 | 39.9 |
| 3 | 73 | 27.9 | 38.1 | 74 | 28.3 | 38.5 |
| 6 | 74 | 27.3 | 36.9 | 74 | 27.3 | 36.9 |
| Mean | 74.0 | 28.4 | 38.4 | 73.6 | 28.4 | 38.4 |
| St. Dev. | 0.7 | 0.9 | 1.0 | 0.5 | 0.7 | 1.1 |

In the table are summarised the values of MCV, MCH and MCHC obtained for RBC loaded with FKBP12 (20, 40 and 80 µM) at the times 0, 1, 2, 3 e 6 days after the treatment compared with those found for unloaded RBC. At the bottom mean values and standard deviations calculated for each sample during the incubation time are reported.

TABLE 3

Encapsulation of rFKBP12 and the total capacity of loaded-erythrocytes to bind FK506 (last right column) and the absolute contribution due to the presence of the recombinant FKBP12 (second last right column)

|  | rFKBP12 Concentration (nmol/ml) RBC 100% Ht) | FK506 concentration (µg/ml) RBC 100% Ht) | Total FK506 concentration (µg/ml) RBC 100% Ht) |
|---|---|---|---|
| Native RBC | 0 | 0 | 1.1 ± 0.4 |
| RBC FKBP12 20 µM | 3.5 ± 2.5 | 2.8 ± 2.0 | 3.9 ± 2.4 |
| RBC FKBP12 40 µM | 7.4 ± 5.4 | 5.9 ± 4.3 | 7.0 ± 4.7 |
| RBC FKBP12 80 µM | 15.5 ± 0.6 | 12.5 ± 0.5 | 13.6 ± 0.9 |

The results showed in the table above are the arithmetical means and the standard deviations of three loading experiments.

Example 2

Cyclophilin-Cyclosporin

Materials and Methods
Manufacturing of a Recombinant Form of Human Cyclophilin A:

a recombinant form of human Cyclophilin A (CypA) has been manufactured as follows. Total RNA was extracted from HeLa cells and cDNA was then obtained by retro-transcription with oligo-dT primer. The cDNA coding for CypA gene (GenBank accession number NM_021130.3) was amplified by PCR with a pair of degenerated primers (Forward 5'-TATT-AGCCCACGTGAACCCCACCGTGTTCTTCG-3' (SEQ ID NO: 4) and Reverse 5'-AACACAAGGGATCCTTATTCGAGTTGTCCAC-3' (SEQ ID NO: 5)) and the amplicon sequenced in both directions with a capillary sequencer to confirm the correct identity of the PCR product. The obtained CypA cDNA was finally digested with BamHI and PmlI and ligated into the pET-45b(+) vector downstream of the poly(histidine) tag coding sequence to produce an N-terminal His-tagged CypA, as reported for FKBP12 manufacturing in the previous example.

```
                                            (SEQ ID NO: 6)
ATGGCACATCACCACCACCATCACGTGAACCCCACCGTGTTCTTCGACAT

TGCCGTCGACGGCGAGCCCTTGGGCCGCGTCTCCTTTGAGCTGTTTGCAG

ACAAGGTCCCAAAGACAGCAGAAAATTTTCGTGCTCTGAGCACTGGAGAG

AAAGGATTTGGTTATAAGGGTTCCTGCTTTCACAGAATTATTCCAGGGTT

TATGTGTCAGGGTGGTGACTTCACACGCCATAATGGCACTGGTGGCAAGT

CCATCTATGGGGAGAAATTTGAAGATGAGAACTTCATCCTAAAGCATACG

GGTCCTGGCATCTTGTCCATGGCAAATGCTGGACCCAACACAAATGGTTC

CCAGTTTTTCATCTGCACTGCCAAGACTGAGTGGTTGGATGGCAAGCATG

TGGTGTTTGGCAAAGTGAAAGAAGGCATGAATATTGTGGAGGCCATGGAG

CGCTTTGGGTCCAGGAATGGCAAGACCAGCAAGAAGATCACCATTGCTGA

CTGTGGACAACTCGAATAA
```

E. coli BL21(DE3) competent cells were transformed with the pET45b-CypA construct and grown in LB medium containing ampicillin (50 μg/ml) at 37° C.; when culture O.D. reached 0.6-0.7, expression of recombinant CypA was induced by standard procedure and growth was continued for a further 2 hours. Induced BL21(DE3) were subsequently homogenized in lysis buffer and the recombinant protein purified to homogeneity through Ni-Affinity chromatography as previously described. Eluted fractions were re-united after SDS-page analysis and dialysed against 2 liters of storage buffer (Tris 20 mM pH 8.0, NaCl 20 mM, DTT 0.5 mM, glycerol 10%). Final purity of recombinant CypA was verified by electrophoresis on 15% acrylamide gel and Coomassie Blue staining and by immunoblotting with mouse anti-histidine tag monoclonal antibody (AbD Serotec, Oxford, UK).

Loading of $I^{125}$-CypA into Human RBC:

recombinant CypA was radio-labelled with sodium 125-iodine via chlorammine-T method to quantify the amount of entrapped protein into erythrocytes. $I^{125}$-CypA (specific activity 695 cpm/μg) was encapsulated into human erythrocytes by means of the procedure of hypotonic dialysis, isotonic resealing and "reannealing" described in the previous example. In particular, human RBC at 70% hematocrit in physiological solution were processed with $^{125}$I-CypA at increasing concentrations (20, 40, 80 μM). Each erythrocyte suspension was dialysed in a separate dialysis tube with 3.5 kDa cut-off, against 50 volumes of hypotonic solution for 90 minutes at 4° C. Erythrocyte resealing was obtained by incubation of processed cells with 0.1 volumes of hypertonic solution and incubation for 25 minutes at 37° C. Loaded cells were treated with hydrogen peroxide and Solvable (Perkin Elmer, Waltham, USA) and subjected to (3-emission counting with Liquid Scintillation Counter (Packard) to quantify the amount of entrapped radioactivity.

Binding Studies rCypA-CsA:

His-tagged CypA (18 kDa) was next investigated for its ability to bind Cyclosporin A (1202.6 amu) by centrifugal fractionation of the protein-drug complex (which remain in the centrifugal filter units, cut-off 10 kDa) from free drug that is recovered in the ultrafiltrate. Briefly, CypA-CsA binding was let occur by incubating protein and drug at a molar ratio of 1:1 for 1 h at 37° C.; successively, the mixture was centrifuged in Amicon Ultra centrifugal filter units (10 kDa) (Millipore, Ireland) according to product instructions. The drug concentration was than detected by HPLC both on the ultrafiltrate and in the rCypA containing solution. A sample containing the CsA molecule alone was filtered in the same manner and used as a control.

Loading of Recombinant CypA into Human Erythrocytes and Evaluation of the CsA Binding Capacity Acquired by CypA-Loaded Erythrocytes:

recombinant CypA has been loaded into human RBC by means of the hypotonic dialysis and isotonic resealing method as reported in the "Loading of $I^{125}$-CypA into human RBC" section. Un-loaded RBC, (i.e. subjected to the same process without addition of the protein) were used as control for the estimation of cell recovery and evaluation of RBC corpuscular indices. CypA-loaded RBC obtained from the loading procedure were then re-suspended in Hepes buffered saline solution at 40% hematocrit and added with CsA to test the RBC binding capacity. CsA (LC Laboratories, Woburn, USA) was dissolved in ethanol (10 mg/ml) and added to cells at the concentration of 20 mg/ml RBC suspension. Cells were incubated for 1 hour at 37° C. in order to permit drug equilibration and then washed with saline buffer to remove un-bound CsA. Un-loaded RBC were used as control during the CsA binding experiment.

Figure 9:
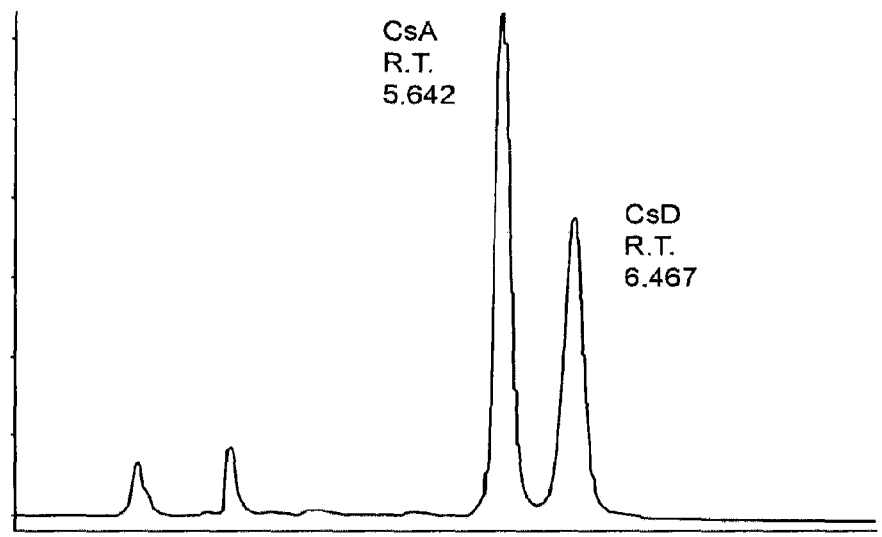
FIG. 9—CsA and CsD UPLC chromatogram. Chromatographic run of standard sample composed of CsA (10 µg/ml) and CsD (10 µg/ml).

HPLC Analysis:

the amount of CsA associated with CypA-loaded and native erythrocytes has been evaluated through a HPLC method preceded by a solid phase extraction (SPE) procedure. In brief, RBC samples obtained at the end of the binding capacity studies were subjected to lysis and de-proteinization with an aqueous $ZnSO_4$ solution and acetone as reported in [Baldelli S 2005[1]. The cleared supernatants were then loaded onto Isolute C18 cartridges (International Sorbent Technology, Tucson, USA) to further cleaning of the extracts. Cyclosporin D (CsD) was used as internal standard during the extraction procedure to evaluate the percentage of recovery of each sample (FIG. 9). The chromatographic runs were performed on C8 columns in isocratic conditions as described in [Baldelli S 2006[1] with some modifications. The analytical column, C8 150×4.6 mm packed with Extrasil 3 μm beads (Teknokroma, BarcelonA, Spain), was heated at 75° C., the mobile phase consisted of 70% $CH_3CN$ in HPLC grade water and was pumped at a flow rate of 0.7 ml/min during the total run length (10 minutes) and the UV detector (Varian 9050, Varian Inc., Palo Alto, USA) was set at 210 nm. Data were processed using a Jasco-Borwin software (Jasco Inc., Easton, USA).

Results and Discussion

Figure 10:
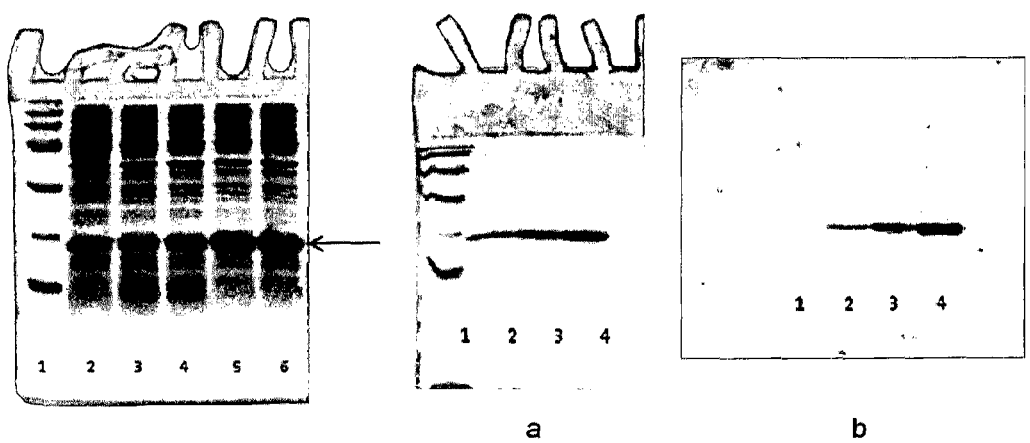
FIG. 10—SDS-PAGE of BL21(DE3) homogenates and SDS-PAGE (a) and immunoblot (b) of purified CypA. Lanes from 1 to 6: Low Molecular Weight standards (LMW), not induced BL21(DE3), BL21(DE3) induced with IPTG for 1, 2, 3 and 4 hours. Total protein extracts (30 µg) obtained from homogenized BL21(DE3) cells were separated on 15% SDS-polyacrylamide gel.

Manufacturing of a Recombinant Form of Human Cyclophilin A:

the recombinant His-tagged CypA was very efficiently expressed in BL21(DE3) *E. coli* strain as demonstrated by FIG. 10 which represents the SDS-PAGE of BL21(DE3) bacterial homogenates. Coomassie Blue stain revealed a protein band of about 18-19 kDa that seems to increase after IPTG induction. In fact, the produced recombinant CypA contains the 8 additional amino acids Met-Ala-(His)$_6$, upstream to the native Cyclophin A protein sequence, where the initiator Met was deleted [Gevaert K 2003, http://www.uniprot.org/blastnabout=P62937[2-28]], and this results in a molecular weight rising of about 1 kDa (from 18 to 19 kDa).

The induced His-tagged CypA has been easily isolated from the bacterial homogenate by Nichel affinity chromatography resulting in a very high yield (about 79 mg per liter of *E. coli* culture). Moreover, the characterization of purified protein through polyacrylamide gel electrophoresis and immunoblotting, showed in FIG. 10, demonstrates an optimal purity level. Indeed, the electrophoretic run of final CypA shows the presence of a single band with an electrophoretic mobility of about 18-19 kDa and a purity level higher than 99%, while the immunoblot certify the identity of the purified protein.

Loading of $I^{125}$-CypA into Human RBC:

at the end of the procedure a rising radioactivity has been recovered in the RBC samples loaded with increasing $^{125}$I-CypA concentrations demonstrating that recombinant CypA can be loaded into human RBC in a dose-dependent way. FIG. 11 shows the increasing intra-erythrocytic concentrations of CypA achieved in the three loading conditions (3.97, 5.00 and 15.85 nmol/ml RBC 100% hematocrit, respectively, for RBC dialysed with CypA 20, 40 and 80 μM).

Binding Studies rCypA-CsA:

the experiments described in the methods section let us to conclude that recombinant CypA is able to bind the CsA ligand. In fact, when CsA has been centrifuged in the presence of CypA more than 70% of the whole drug was recovered in the un-filtered fraction, while when CsA has been centrifuged alone, only 15% of cyclosporine was found in the upper portion, suggesting that the drug is retained owing to the binding with the protein. So the presence of the poly (histidine) tag seems not to compromise the protein functionality.

Characterization of rCypA-Loaded RBC:

concerning the production of engineered RBC with higher amounts of intra-cellular cyclophilin, an optimal cell recovery was obtained for CypA-loaded RBC resulting respectively 67, 69 e 67 percent for dialysed RBC incubated with CypA 20, 40 e 80 μM, clearly similar to that got for erythrocytes dyalised in the absence of the protein (68%). These data demonstrate that cell recovery is not affected of by presence and concentration of CypA. Also the evaluation of RBC corpuscular indices (MCV, MCH, MCHC) revealed values for CypA-loaded erythrocytes in good agreement with those of un-loaded (UL) cells (Table 2).

Evaluation of the Cyclosporin a Binding Capacity Acquired by CypA-Loaded Erythrocytes:

CypA-loaded and un-loaded RBC were finally investigated for their binding capacity versus Cyclosporin. Cells have been incubated with the drug and then processed for the quantification of CsA levels through HPLC analysis. The results illustrated by the histogram in FIG. 11 demonstrate that CypA-loaded erythrocytes were able to bind higher amounts of CsA compared with unloaded cells and that the quantity of drug associated with loaded RBC depends on the protein concentration added during the dialysis step. Actually, RBC dialysed with 20, 40 and 80 μM CypA were demonstrated to be able to bind a drug amount equivalent to 8.9, 12.2 and 17.0 μg/ml RBC at 100% hematocrit, respectively, while un-loaded RBC were able to carry only 3.3 μg CsA per milliliter of packed RBC. By comparing the results showed above with those reported in literature for native erythrocytes ($43 \times 10^{-5}$ nmol CsA per $10^6$ RBC [Foxwell B M 1988, Reichel C 1994$^1$, that is equivalent to 5 μg CsA per milliliter of packed RBC) it becomes evident that CypA-loaded RBC possess a clearly higher binding capacity for CsA in all loading conditions.

In conclusion, the data now exposed, demonstrate that:

1) it is possible encapsulate CypA into human erythrocytes;
2) the encapsulation is dose-dependent; and
3) higher CypA entrapment corresponds to a higher intraerythrocytic CsA concentration; indeed, red blood cells loaded with increasing CypA quantities (20, 40 and 80 μM) were able to bind a quantity of drug 3, 4 and 5 times greater than un-loaded cells and 1.8, 2.4 and 3 times greater compared with native cells.

TABLE 4

Corpuscolar indices of CypA-loaded RBC versus un-loaded RBC and native RBC

|    | MCV       | MCH         | MCHC         |
|----|-----------|-------------|--------------|
| ND | 90 ± 2.1  | 34.1 ± 1.0  | 38.1 ± 1.3   |
| UL | 80 ± 2.2  | 28.7 ± 0.9  | 36.0 ± 1.1   |
| L1 | 78 ± 1.9  | 28.1 ± 0.8  | 36.1 ± 0.9   |
| L2 | 79 ± 2.1  | 28.0 ± 1.1  | 35.7 ± 1.5   |
| L3 | 77 ± 3.9  | 27.3 ± 1.6  | 35.6 ± 1.3   |

In the table are compared the MCV, MCH and MCHC values shown by CypA-loaded RBC with those of un-loaded and native cells. The reported values are means and standard deviations from four loading experiments.

References for Example 2

1. Dunn C J, Wagstaff A J, Perry C M, Plosker G L, Goa K L. Cyclosporin: an updated review of the pharmacokinetic properties, clinical efficacy and tolerability of a microemulsion-based formulation (neoral)1 in organ transplantation. Drugs 2001; 61(13):1957-2016.
2. Faulds D, Goa K L, Benfield P. Cyclosporin. A review of its pharmacodynamic and pharmacokinetic properties, and therapeutic use in immunoregulatory disorders. Drugs 1993; 45(6):953-1040.
3. Pollard S, Nashan B, Johnston A, Hoyer P, Belitsky P, Keown P, Helderman H. A pharmacokinetic and clinical review of the potential clinical impact of using different formulations of cyclosporin A. Berlin, Germany, Nov. 19, 2001. Clin Ther. 2003; 25(6):1654-1669.
4. Cattaneo D, Perico N, Remuzzi G. From pharmacokinetics to pharmacogenomics: a new approach to tailor immunosuppressive therapy. Am. J. Transplant. 2004; 4(3):299-310.
5. Naesens M, Kuypers D R, Sarwal M. Calcineurin inhibitor nephrotoxicity. Clin J. Am. Soc. Nephrol. 2009; 4(2):481-508.
6. Foxwell B M, Frazer G, Winters M, Hiestand P, Wenger R, Ryffel B. Identification of cyclophilin as the erythrocyte ciclosporin-binding protein. Biochim. Biophys. Acta Mar. 3, 1988; 938(3):447-455.
7. Reichel C, von F M, Brockmeier D, Dengler H J. Characterization of cyclosporine A uptake in human erythrocytes. Eur. J Clin Pharmacol. 1994; 46(5):417-419.
8. Baldelli S, Murgia S, Merlini S, Zenoni S, Perico N, Remuzzi G, Cattaneo D. High-performance liquid chromatography with ultraviolet detection for therapeutic drug monitoring of everolimus. J. Chromatogr. B Analyt. Technol. Biomed. Life Sci. Feb. 25, 2005; 816(1-2):99-105.
9. Baldelli S, Zenoni S, Merlini S, Perico N, Cattaneo D. Simultaneous determination of everolimus and cyclosporine concentrations by HPLC with ultraviolet detection. Clin Chim. Acta 2006; 364(1-2):354-358.
10. Gevaert K, Goethals M, Martens L, Van D J, Staes A, Thomas G R, Vandekerckhove J. Exploring proteomes and analyzing protein processing by mass spectrometric identification of sorted N-terminal peptides. Nat. Biotechnol. 2003; 21(5):566-569.

The invention claimed is:

1. A red blood cell modified to comprise enhanced levels of a protein, wherein the protein is capable of forming an association complex with a drug, wherein the uncomplexed form of the drug is capable of passing the red blood cell membrane, wherein the uncomplexed protein cannot pass the red blood cell membrane; and,
  wherein the modified red blood cell comprises at least 3.5-fold more of the protein inside the cell membrane than an unmodified red blood cell.

2. The red blood cell of claim 1, wherein the protein is FKBP12 and the drug is Tacrolimus (FK506) or Rapamycin.

3. The red blood cell of claim 1, wherein the protein is Cyclophilin and the drug is Cyclosporine.

4. The red blood cell of claim 1, wherein the protein is an immunophillin and the drug is an associated immunosuppressant or antiviral capable of binding said immunophillin.

5. The red blood cell of claim 4, wherein the immunosuppressant is capable of inhibiting the activation of the phosphatase calcineurin by forming a complex with calcineurin and the immunophillin.

6. The red blood cell of claim 4, wherein the immunophillin is selected from FKBP12 or its analogues.

7. The red blood cell of claim 4, wherein the immunophillin is selected from cyclophilin or its analogues.

8. The red blood cell of claim 4, wherein the immunosuppressant is a Calcineurin inhibitor.

9. The red blood cell of claim 8, wherein the Calcineurin inhibitor is FK506 (Tacrolimus).

10. The red blood cell of claim 8, wherein the Calcineurin inhibitor is Cyclosporine.

11. The red blood cell of claim 1, wherein the red blood cell is blood group O and Rhesus negative.

12. A red blood cell modified to comprise enhanced levels of a protein that cannot pass the red blood cell membrane, wherein the protein is capable of forming an association complex with a drug, the uncomplexed form of the drug being capable of passing the red blood cell membrane, and wherein the modified red blood cell comprises at least 3.5-fold more of the protein than an unmodified red blood cell, the protein being selected from the group consisting of FKBP12, cyclophilin, and immunophillin.

13. A method for the treatment of cancer or vial infections comprising administering the red blood cell of claim 1 to a patient in need thereof.

14. A method of immunosuppression comprising administering the red blood cell of claim 12 to a patient requiring immunosuppression.

15. A method of reducing the concentration of a drug in a patient's body fluid, preferably the plasma, comprising administering the red blood cells of claim 1 to a patient in need thereof
  wherein the protein is a recombinant protein capable of forming an association complex with the drug.

16. The red blood cell of claim 12, wherein the target drug is selected from the group consisting of: Tacrolimus (FK506), Rapamycin, Cyclosporine, an immunosuppressant associated with immunophillin, and an antiviral capable of binding immunophillin.

17. The red blood cell of claim 1, wherein not more than 50% of the uncomplexed protein passes through the red blood cell membrane per 24 hours.

18. The red blood cell of claim 1, wherein the red cell contains at least 5 ug/ml of the protein.

19. The red blood cell of claim 1, wherein the protein is a non-native protein.

20. The red blood cell of claim 1, wherein the unmodified red blood cell is an unloaded control from the same blood sample as the modified red blood cell.

* * * * *